US00PP26434P3

(12) United States Plant Patent
Keogh

(10) Patent No.: US PP26,434 P3
(45) Date of Patent: Mar. 1, 2016

(54) **VARIETY OF *TIBOUCHINA* NAMED 'PMA TIB 2'**

(50) Latin Name: *Tibouchina mutabilis*
Varietal Denomination: PMA Tib 2

(71) Applicant: Terry Keogh, Victoria Point (AU)

(72) Inventor: Terry Keogh, Victoria Point (AU)

( * ) Notice: Subject to any disclaimer, the term of this patent is extended or adjusted under 35 U.S.C. 154(b) by 179 days.

(21) Appl. No.: 13/815,692

(22) Filed: Mar. 14, 2013

(65) Prior Publication Data

US 2014/0283247 P1 Sep. 18, 2014

(51) Int. Cl.
*A01H 5/02* (2006.01)

(52) U.S. Cl.
USPC ..... Plt./226
CPC ..... *A01H 5/02* (2013.01)

(58) Field of Classification Search
USPC ..... Plt./226
See application file for complete search history.

(56) References Cited

PUBLICATIONS

U.S. Trademark for 'Imagine', serial No. 77680182, registration date May 20, 2011.*

* cited by examiner

*Primary Examiner* — Anne Grunberg
(74) *Attorney, Agent, or Firm* — The Webb Law Firm

(57) ABSTRACT

'PMA Tib 2' is a new variety of *Tibouchina* plant that is suitable for planting in gardens, containers, and in landscaping having mauve/purple flowers that darken through maturity, a domed and dense plant habit, and medium-sized flowers.

2 Drawing Sheets

Botanical classification: *Tibouchina mutabilis.*
Varietal denomination: 'PMA TIB 2'.

BACKGROUND OF THE NEW PLANT

The present invention comprises a new and distinct cultivar of *Tibouchina* plant, botanically known as *Tibouchina mutabilis* and hereinafter referred to by the cultivar name 'PMA Tib 2'.

The new and ornamental variety was selected by the breeder as a result of an ongoing breeding program that has been conducted by the inventor for more than thirty years at the inventor's nursery in Victoria Point, Queensland, Australia. The purpose of the breeding program is to produce novel varieties of *Tibouchina* in varying plant sizes, flower colors, and which are well-suited to a range of climate zones. 'PMA Tib 2' is a hybrid plant derived from the deliberate controlled cross-pollination of the unpatented female parent, an individual plant of *Tibouchina mutabilis,* named 'Noelene', and the unpatented male parent, an individul plant of *Tibouchina mutabilis* named 'Jazzie'. The inventor emasculated flowers of the female parent and applied pollen that was freshly collected from the male parent in 2003. The parent plants were isolated to prevent open pollination. In 2005, the inventor selected 'PMA Tib 2' as a seedling that had been raised from the cross-pollination described herein. Selection was based on the criteria of habit, flower color, and plant dimensions. The plant was then propagated in 2008 via vegetative cuttings to produce a new generation for final evaluation.

Further, asexual reproductions of 'PMA Tib 2' in Victoria Point, Queensland, Australia has demonstrated that the combination of characteristics as herein disclosed for the new cultivar are retained and reproduced true to type through more than six successive generations of asexual reproduction.

The color references made herein are to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'PMA Tib 2' which, in combination, distinguish this *Tibouchina* plant as a new and distinct cultivar:

1. Medium-sized shrub with a domed plant habit at maturity;
2. Dense plant habit;
3. Pale mauve/purple flowers that change to medium mauve/purple towards the margin when the flowers first open—the flowers turn completely medium mauve/purple at maturity;
4. Medium flower size;
5. Large volume of flowers; and
6. Woody, long-lived shrub.

The new variety differs from 'Noelene' and 'Jazzie' in its smaller, mature plant size. Additionally, the flower color change of 'PMA Tib 2' as aging occurs is more distinct than with 'Noelene'.

When compared to 'PMA Tib 1' (U.S. Plant patent application Ser. No. 13/815,685), 'PMA Tib 2' has a smaller flower size and plant dimensions. The petals do not overlap as significantly with 'PMA Tib 2'.

When 'PMA Tib 2' is compared to 'Chameleon' (unpatented), the distinct margin color and predominately white petal color of a newly opened flower are not as prominent as 'PMA Tib 2'. Further, 'Chameleon' exhibits more upright mature plant dimensions than 'PMA Tib 2'.

BRIEF DESCRIPTION OF THE DRAWINGS

The accompanying photographic drawings illustrate the new variety, with the colors being as nearly true as is possible with color illustrations of this type.

PROPAGATION

Figure 1:
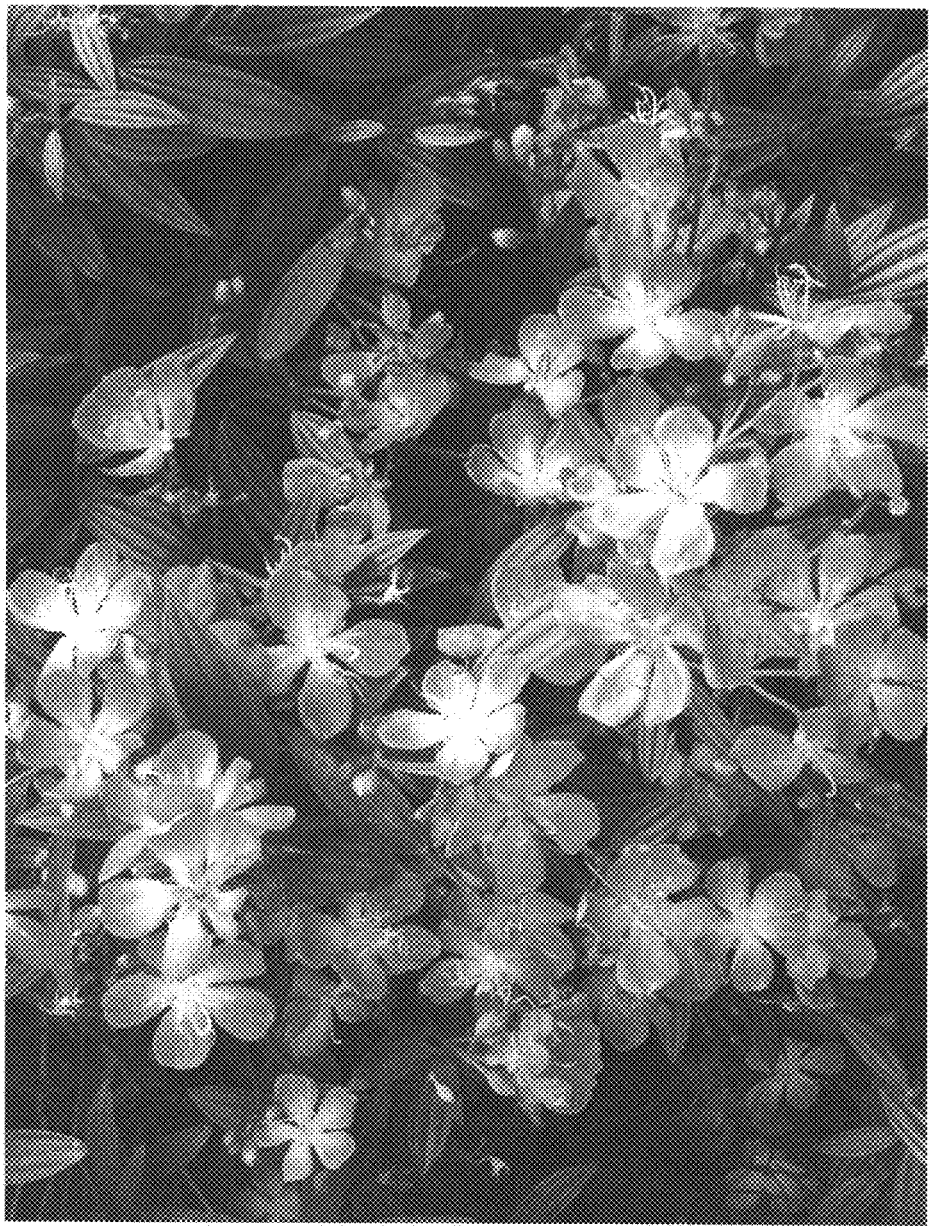
FIG. 1 is close-up photograph of the flowers of the new variety.
Figure 2:
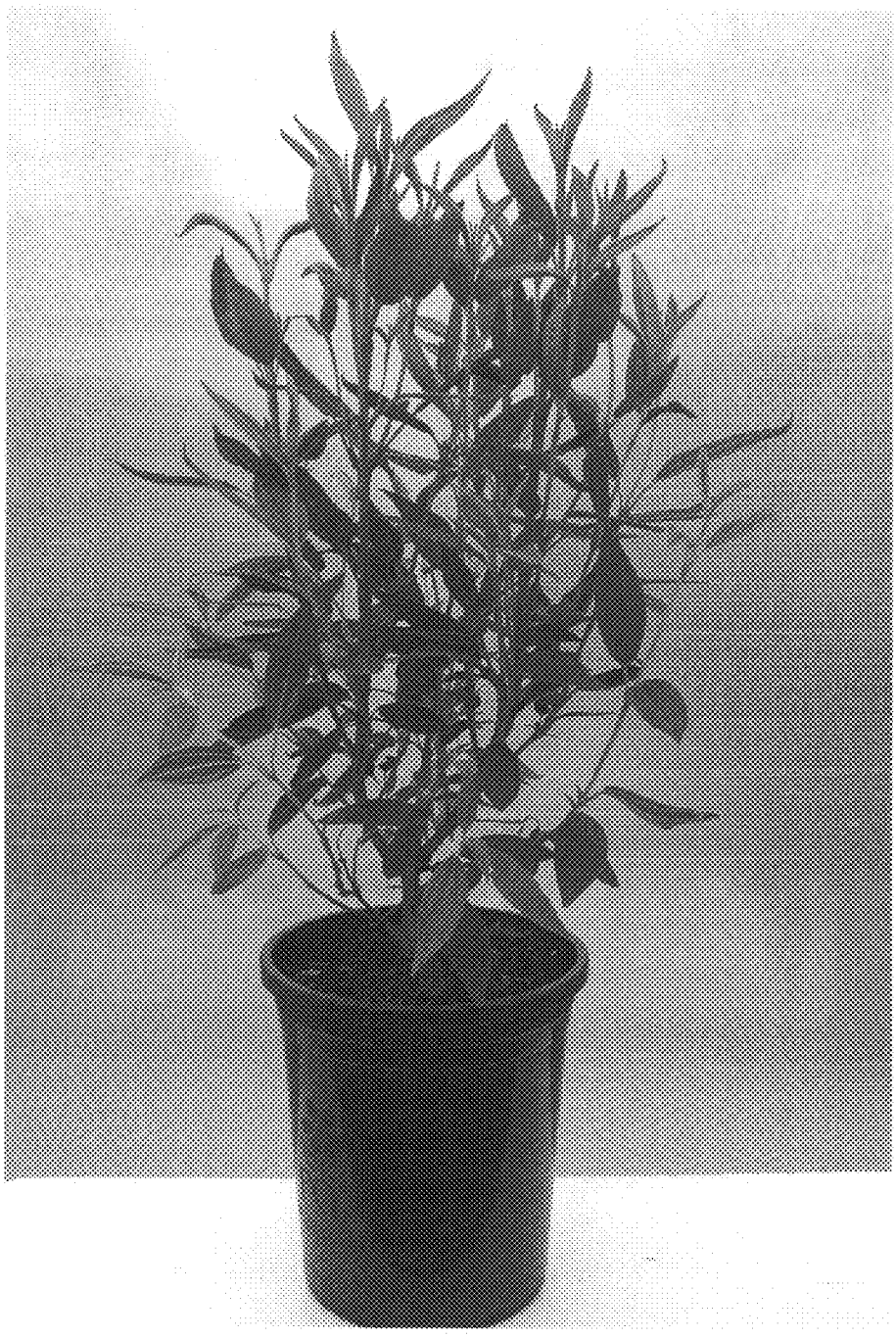
FIG. 2 is a photograph of an entire plant of the new variety

*Time to initiate roots.*—About 14-18 days at approximately 21° C.

*Time to produce a rooted cutting.*—About 24-30 days at 21° C.

PLANT

*Plant spread.*—Approximately 27 cm.

*Plant height.*—40 cm.

*Growth rate.*—Medium to fast.

*Lateral branches.*—Length: Approximately 30 cm. Diameter: Approximately 0.22 cm. Quantity: About 30.

*Age of plant when described.*—Approximately 16 weeks from a rooted cutting.

*Growth habit.*—Upright to bushy.

*Height at maturity.*—1.5 m.

*Width at maturity.*—1.5 m.

Stem:

*Branching habit.*—Strong; upright when juvenile.

*Main stem diameter.*—0.85 cm.

*Lateral stem length (average).*—15 cm.

*Lateral stem width (average).*—0.22 cm.

*Internode length (range).*—1.4 cm to 7.7 cm.

*Shape.*—Square in cross section.

*Surface.*—Rough.

*Branch color.*—Juvenile: N144D. Semi-ripe: 146C. Mature: N199D.

Foliage:

*Leaf.*—Arrangement: Opposite. Division: Simple. Margin: Entire. Shape: Elliptic. Base: Cuneate. Apex: Acute to acuminate. Surface (adaxial): Pubescent. Surface (abaxial): Pubescent. Texture (adaxial surface): Weakly ribbed with a matte surface. Texture (abaxial surface): Prominently ribbed. Attachment: Petiolate. Length (range excluding petiole): 2.5 cm to 7.5 cm. Width (range): 0.85 cm to 2.6 cm. Color (adaxial surface): 147A. Color (abaxial surface): 146B. Color of juvenile foliage not fully expanded: 146C.

*Foliar fragrance.*—None observed to date.

*Venation.*—Pattern: Reticulate; 3 primary parallel veins. Color (adaxial surface): 146B. Color (abaxial surface): 146C. Prominence (adaxial surface): Depressed. Vein prominence (abaxial surface): Raised.

*Petiole.*—Length (range): 0.7 cm to 2.6 cm. Diameter (average): 0.13 cm. Color: N144D and 178B. Surface: Pubescent. Shape: Cylindrical, but flattened on the adaxial surface.

Flower:

*Shape.*—Rotate.

*Aspect.*—Facing upward and outward.

*Inflorescence type.*—Solitary.

*Persistent or self-cleaning.*—Self-cleaning.

*Blooming period.*—Summer through fall; can bloom sporadically during other times.

*Inflorescence fragrance.*—None observed to date.

*Petals.*—Number: 5. Central color (both surfaces): 77B. Margin color (both surfaces): 75A. Central color as senesces: 80C. Margin: Entire and weakly undulating. Apex: Obtuse to broadly acute. Base: Broadly attenuate. Shape: Obovate to elliptic. Surface (abaxial and adaxial): Glabrous. Fused or unfused: Unfused. Petals overlapping: Absent.

*Buds.*—Color: 79C. Shape: Elliptic. Apex: Acute.

*Calyx.*—Color: 34C. Shape: Cupule.

*Sepals.*—Color (adaxial surface): 135D. Color (abaxial surface): 175D. Quantity: 5 in number. Margin: Entire. Base: Truncate. Fused or unfused: Unfused.

*Peduncle.*—Color: 145B. Shape: Cylindrical.

Reproductive organs:

*Stamens.*—Number: Usually 10 in number (5 long and 5 short). Color at flower first opening: 81A. Color at flower senescence: 38D.

*Anthers.*—Color at flower first opening: 65B. Color at flower senescence: 68B. Shape: Sickle.

*Pollen.*—None observed.

*Pistil.*—Number: 1. Shape: Columnar and curved at the end. Color at flower first opening: 142B. Color at flower senescence: 157C.

*Stigma.*—Color: 157C. Shape: Flattened.

*Ovary.*—Color: 159A. Shape: Cupule. Position: Inferior.

*Seeds.*—No seeds have been observed to date.

I claim:

1. A new and distinct variety of *Tibouchina* plant named 'PMA Tib 2' as herein described and illustrated.

* * * * *

UNITED STATES PATENT AND TRADEMARK OFFICE

CERTIFICATE OF CORRECTION

PATENT NO. : PP26,434 P3
APPLICATION NO. : 13/815692
DATED : March 1, 2016
INVENTOR(S) : Terry Keogh It is certified that error appears in the above-identified patent and that said Letters Patent is hereby corrected as shown below:

Specification

Column 1, Line 21, delete "individul" and insert -- individual --

Signed and Sealed this
Twenty-eighth Day of June, 2016

Michelle K. Lee

Michelle K. Lee
*Director of the United States Patent and Trademark Office*